US010607344B2

(12) United States Patent
Hueber et al.

(10) Patent No.: US 10,607,344 B2
(45) Date of Patent: Mar. 31, 2020

(54) IMAGE DATA TRANSFER SYSTEM, CONNECTION NODE, MEDICAL WORK AREA AND METHOD FOR TRANSFERRING IMAGE DATA AND FOR CONFIGURING AN IMAGE DATA TRANSFER SYSTEM

(71) Applicant: OLYMPUS WINTER & IBE GMBH, Hamburg (DE)

(72) Inventors: Mathias Hueber, Hamburg (DE); Sascha Jaskola, Hamburg (DE); Juri Sverdlov, Hamburg (DE); Ralf Tessmann, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 181 days.

(21) Appl. No.: 15/850,335

(22) Filed: Dec. 21, 2017

(65) Prior Publication Data

US 2018/0137619 A1 May 17, 2018

Related U.S. Application Data

(63) Continuation of application No. PCT/EP2016/064819, filed on Jun. 27, 2016.

(30) Foreign Application Priority Data

Jul. 16, 2015 (DE) .......... 10 2015 213 383

(51) Int. Cl.
*G06K 9/00* (2006.01)
*G06T 7/00* (2017.01)
(Continued)

(52) U.S. Cl.
CPC ........ *G06T 7/0012* (2013.01); *A61B 1/00011* (2013.01); *A61B 6/563* (2013.01);
(Continued)

(58) Field of Classification Search
CPC combination set(s) only.
See application file for complete search history.

(56) References Cited

U.S. PATENT DOCUMENTS 5,954,650 A * 9/1999 Saito ................ G06T 11/00
382/128
6,246,432 B1 6/2001 Takami et al.
(Continued)

FOREIGN PATENT DOCUMENTS

| DE | 10056178 A1 | 5/2001 |
| EP | 0881834 A2 | 12/1998 |
| WO | 2014163109 A1 | 10/2014 |

OTHER PUBLICATIONS

International Search Report dated Sep. 16, 2016 issued in PCT/EP2016/064819.

*Primary Examiner* — Alex Kok S Liew
(74) *Attorney, Agent, or Firm* — Scully, Scott, Murphy & Presser, P.C.

(57) ABSTRACT

An image data transfer system including: at least one image data source; at least one image data sink; and a connection node; wherein the connection node is coupled to the image data source and the image data sink via at least one data connection; the image data source is configured to provide image data in at least two different data formats; the image data sink is configured to process image data in one of the at least two data formats; and the connection node is configured to receive information relating to a selection of the image data sink and to establish a data transfer path between a selected image data sink and the image data source, the data transfer path being configured in that, from the image data source, image data is provided to the selected image data sink in the data format of the selected image data sink.

14 Claims, 1 Drawing Sheet

(51) Int. Cl.
  *H04N 7/18*    (2006.01)
  *A61B 1/00*    (2006.01)
  *H04N 5/268*   (2006.01)
  *A61B 6/00*    (2006.01)

(52) U.S. Cl.
  CPC ............ *H04N 5/268* (2013.01); *H04N 7/181* (2013.01); *A61B 1/00193* (2013.01); *G06T 2200/04* (2013.01); *G06T 2207/10012* (2013.01); *G06T 2207/10068* (2013.01); *G06T 2210/41* (2013.01)

(56) References Cited

U.S. PATENT DOCUMENTS

| | | |
|---|---|---|
| 6,858,004 B1 | 2/2005 | Ozawa et al. |
| 2003/0142119 A1* | 7/2003 | Akagi .................. A61B 6/4216 345/698 |
| 2003/0197781 A1 | 10/2003 | Sugimoto et al. |
| 2009/0086018 A1* | 4/2009 | Shim ...................... A61B 1/041 348/68 |
| 2011/0157605 A1* | 6/2011 | Pepin ...................... H04N 1/58 358/1.2 |
| 2013/0246576 A1 | 9/2013 | Wogsberg et al. |
| 2016/0029011 A1 | 1/2016 | Mizoguchi et al. |

\* cited by examiner

IMAGE DATA TRANSFER SYSTEM, CONNECTION NODE, MEDICAL WORK AREA AND METHOD FOR TRANSFERRING IMAGE DATA AND FOR CONFIGURING AN IMAGE DATA TRANSFER SYSTEM

CROSS-REFERENCE TO RELATED APPLICATION

The present application is a continuation of PCT/EP2016/064819 filed on Jun. 27, 2016, which is based upon and claims the benefit to DE 10 2015 2133 83.4 filed on Jul. 16, 2015, the entire contents of each of which are incorporated herein by reference.

BACKGROUND

Field

The present disclosure relates to an image data transfer system comprising at least one image data source, at least one image data sink and a connection node, wherein the connection node is coupled to the image data source and the image data sink via at least one data connection respectively, the image data source is configured to provide image data in at least two data formats that are different from one another, and the image data sink is configured to process image data in one of the data formats.

The present disclosure further relates to a connection node in an image data transfer system which, in addition to the connection node, comprises at least one image data source and at least one image data sink, wherein the connection node is/can be coupled to the image data source via at least two input-side interfaces and to the image data sink via at least one output-side interface, wherein the at least two input-side interfaces are configured to receive image data in two data formats that are different from one another, which is/can be provided from the image data source coupled to the respective interface, and the at least one output-side interface is configured to provide image data in an image data format of the image data sink, wherein the image data sink is configured to process image data of this data format.

The present disclosure likewise relates to a medical work area comprising such an image transfer system as well as a method for transferring image data, such as in a medical work area, between an image data source and at least one image data sink, wherein the image data source is coupled to the image data sink via a connection node, and the image data source provides image data in at least two data formats that are different from one another, and the image data sink processes image data in one of the data formats.

The present disclosure further relates to a configuration method for configuring an image data transfer system, such as in a medical work area, wherein the image data transfer system comprises at least one image data source, at least one image data sink and a connection node, the connection node is coupled to the image data source and the image data sink via at least one data connection respectively, the image data source is configured to provide image data in at least two data formats that are different from one another, and the image data sink is configured to process image data in one of the data formats.

Still further, the present disclosure relates to a computer program product.

Prior Art

A plurality of image data sources and image data sinks can be found in modern medical work areas. Image data sources are, for example, endoscopes, microscopes and video cameras for documenting images of an examination or operation. Likewise, imaging medical devices, for example, X-ray devices, CT scanners, magnetic resonance imaging systems and the like can be provided as image data sources. Image data sinks are, for example, monitors or projectors, with the aid of which static or moving images are reproduced, both as a 2D and a 3D representation. The plurality of source and target formats of the different image data sources and image data sinks which are present in such an environment frequently present the medical staff with the time-consuming task of combining the desired image data sources and image data sinks with one another such that appropriately supported image formats exist on both sides. In other words, the suitable reproducing unit must also be found for each image data source (and vice versa) and connected thereto so that images are reproduced without any errors.

SUMMARY

An object is to indicate an image data transfer system, a connection node in an image data transfer system, a medical work area, a method for transferring image data and for configuring an image data transfer system and a computer program product, in which an objective is to simplify the technically correct allocation between image data sources and image data sink.

Such object can be solved by an image data transfer system comprising at least one image data source, at least one image data sink and a connection node, wherein the connection node is coupled to the image data source and the image data sink via at least one data connection respectively, the image data source is configured to provide image data in at least two data formats that are different from one another, and the image data sink is configured to process image data in one of the data formats, wherein the connection node can be configured to receive information relating to a selection of the image data sink, and to establish a data transfer path between the selected image data sink and the image data source, wherein the data transfer path is configured in that, from the image data source, image data is/can be provided to the image data sink in the data format of the selected image data sink.

Image data sinks constantly support a limited number of different image formats, in many cases merely one particular image format. If the image data sink supports multiple image formats, a changeover or selection frequently has to be made manually, for example, by selecting and connecting a corresponding input interface. The image data transfer system can make it possible to simply select the desired image data sink; the suitable and correct output of the image data source is automatically selected. In other words, the user of the image data transfer system does not therefore have to worry about image formats and image data sources and sinks which are compatible with one another. He or she makes a selection on the basis of the desired image data sink. The image data transfer system can automatically assume the task of making the associated technically correct selection of the associated or respectively suitable output of the image data source.

This functionality considerably simplifies the operation of the image data transfer system. The image data transfer system is therefore very easy to operate. The possibility of it being operated incorrectly is practically excluded. In addition to a high degree of reliability, the system therefore also offers a great deal of convenience and, in addition, only requires a small amount of technical expertise on the part of the user.

According to an embodiment, the image data source can comprise at least two interfaces, to which the image data is/can be provided in one of the at least two data formats that are different from one another respectively, wherein the connection node comprises input-side interfaces, which are coupled to the interfaces of the image data source via data connections, and output-side interfaces, to which the at least one image data sink is coupled via at least one data connection, wherein the connection node is configured to establish an internal data connection between the output-side interface coupled to the selected image data sink and that input-side interface, to which image data in the data format of the selected image data sink is/can be provided from the image data source.

Image data sources are in many cases configured to provide image data in multiple formats. The corresponding image data format is typically provided to different interfaces of the image data source. Thus, the allocation between the image data source and the image data sink or respectively the technically suitable allocation of the formats is carried out by selecting the suitable interface of the image data source. The connection node establishes a corresponding internal data connection between the appropriate input-side and output-side interfaces. The image data signals or respectively the image data stream from the input-side interface are thus placed on the output-side interface.

An image data source can comprise multiple physical units. For example, a first physical unit which provides 2D image data, and a second physical unit which provides 3D image data can be provided. The physical units can be, for example, supplied with image data of a corresponding camera head.

If, conversely, the image data sink is also to be configured to reproduce image data in different formats, an allocation between the suitable interface of the image data sink and a suitable interface of the image data source can also be established on the part of the image data sink.

Within the context of the formulations indicated above, a monitor acting as an image data sink which is designed to reproduce image data in different data formats can be regarded as two image data sinks. The two image data sinks can be, for example, the two input tuners or units, which process the image data of different formats and which are simply arranged in a joint housing or respectively integrated into such a joint device. The units can share joint usable hardware elements, for example the LCD or LED display.

The at least one first and one second image data sink can be comprised, wherein the first image data sink is configured to process image data in a first data format, and the second image data sink is configured to process image data in a second data format that is different from the first data format, wherein the connection node is configured to receive information relating to a selection of the first or the second image data sink and to establish a data transfer path between the selected first or second image data sink and the image data source, wherein the data transfer path is configured in such a way that, from the image data source, image data is/can be provided to the image data sink in the data format of the selected image data sink.

According to another embodiment, the image data sink can be an image data reproducing unit and/or an image data memory and/or an image data processing unit.

The image data reproducing unit can be a screen, e.g. a LED or LCD flat screen or a projector. The image data processing unit can be, for example, a computer or respectively a workstation, which is equipped with the relevant software so that the image data received can be further processed.

The image data source can be configured to provide 2D and/or 3D image data of moving and/or non-moving images. Such an image data source can be, for example, a 3D video endoscope which, in addition to 3D image data (stereoscopic image data), also supplies 2D image data. Such a device provides photo and video data, wherein different resolutions of the image data can additionally be offered. The at least one image data sink, for example a monitor, can then be configured, for example, to optionally process 2D or 3D image data of moving and/or non-moving images. In accordance with the selection of the monitor, the suitable output of the endoscope can be switched through so that an error-free image reproduction is ensured.

Further image data formats can be, for example, formats which have an image resolution of varying degrees or respectively a different number of pixels, for example, HD or 4K. The image data of non-moving images can be, for example, photos or image data of an imaging medical device, for example an X-ray device, CT scanner, magnetic resonance imaging system, etc. Image data of moving images can be, for example, video image data, such as a video image data stream. 3D image data can also be referred to as stereoscopic image data and can be provided by both imaging methods and by corresponding stereo cameras, which act as an image data source.

Image data sinks can be present in the image data transfer system, which can be configured to reproduce more than one image data format. For example, many flat screens can be configured to reproduce both 2D and 3D image data. If the image data source then, in addition, makes both 2D and 3D image data available, no clear allocation is made, based on the selection of the image data sink, regarding which format the image data source provides to the selected image data sink. This selection can be made in an additional step. Within the context of the construction of the image data transfer system, the image data formats of the image data source and image data sink can be compatible with one another. This would apply in the example indicated above to both the 2D and the 3D image data. The situation is different if an image data sink is selected which is simply configured, for example, to reproduce 2D image data. Such an image data sink can be, for example, a flat screen of a slightly older type. If this image data sink is selected, then, in the case of an image data source which provides both 2D and 3D image data, that output is selected, to which the 2D image data is provided, so that the formats of the image data source and the image data sink technically match one another.

The image data transfer system can be used in accordance with other aspects in a medical environment, such as in a medical work area. According to embodiment, the image data transfer system can be developed in that the image data source is a medical device, such as a surgical instrument, an endoscope or a stereo endoscope.

The medical device can be a medical device with which an imaging examination method can be performed, for example an endoscope or a microscope, but also an X-ray device, CT scanner, magnetic resonance imaging system and the like. The medical device can be a stereo endoscope which provides both 2D image data and 3D image data.

Such object can also be solved by a connection node in an image data transfer system which, in addition to the connection node, comprises at least one image data source and at least one image data sink, wherein the connection node is/can be coupled to the image data source via at least two input-side interfaces and to the image data sink via at least one output-side interface, wherein the at least two input-side interfaces are configured to receive image data in two data formats that are different from one another, which is/can be provided from the image data source coupled to the respective interface, and the at least one output-side interface is configured to provide image data in a data format of the image data sink, wherein the image data sink is configured to process image data of this data format, wherein the connection node is developed in that information relating to a selection of the image data sink is available in the connection node and the connection node can be configured to establish an internal data connection between the output-side interface, to which the selected image data sink is coupled, and the input-side interface, to which image data from the image data source is/can be provided in the data format of the selected image data sink.

The connection node can comprise a switching matrix and control unit. The switching matrix can establish the physical connection between the input-side interface(s) and the output-side interface(s). The switching matrix can be controlled by the control unit so that the switching matrix provides the relevant internal data connections. The control unit can also be realized by software means. These software means can be, for example, run on an external computer which is connected to the switching matrix.

The same or similar advantages as have already been mentioned with respect to the image data transfer system apply to the connection node so that these is shall not be reiterated here.

Such object can also be solved by a medical work area comprising an image data transfer system according to one or more of the indicated aspects and having a medical device, such as a surgical instrument, an endoscope and a stereo endoscope as the image data source.

A plurality of image data sources can be provided in modern medical work areas. These are, for example, the previously mentioned medical devices or surgical instruments, such as imaging endoscopes. An allocation between the corresponding outputs or respectively interfaces of these devices and the associated image data sinks, for example screens present in the medical work area, presents the medical staff with huge challenges in many cases. Technically trained staff having a relatively high level of expertise are needed to constantly provide the desired image information in a reliable manner. With the present image data transfer system it is simply necessary to select the desired image data sink, for example a particular monitor. The work flow in the medical work area is improved and simplified. The medico cal staff is again in a position to concentrate on their actual tasks and what is important in their work.

Such object is further solved by a method for transferring image data, such as in a medical work area, between an image data source and at least one image data sink, wherein the image data source is coupled to the image data sink via a connection node, and the image data source provides image data in at least two data formats that are different from one another, and the image data sink processes image data in one of the data formats, wherein information relating to a selection of the image data sink is available in the connection node and a data transfer path between the selected image data sink and the image data source is established, wherein the data transfer path is configured in such a way that, from the image data source, image data is provided to the image data sink in the data format of the image data sink.

The information relating to the selection of the image data sink is received by the connection node, for example by a user unit or also by another point.

The same or similar advantages as have already been mentioned with respect to the image data transfer system also apply to the method.

The image data source, in such method, can comprise at least two interfaces, to which the image data is provided in one of the at least two data formats is that are different from one another respectively, wherein the connection node can comprise input-side interfaces, which can be coupled to the interfaces of the image data source via at least one data connection respectively, and output-side interfaces, to which the at least one image data sink is coupled via at least one data connection, and wherein the connection node establishes an internal data connection between the output-side interface connected to the selected image data sink and that input-side interface, to which image data in the data format of the selected image data sink is provided from the image data source.

In such method, where at least one first and one second image data sink are present, the first image data sink processes image data in a first data format and the second image data sink processes image data in a second data format that is different from the first data format, the connection node can receive information relating to a selection of the first or the second image data sink and establish a data transfer path between the selected first or second image data sink and the image data source, wherein the data transfer path can be configured in such a way that, from the image data source, image data is/can be provided to the image data sink in the data format of the selected image data sink.

Such object can also be solved by a configuration method for configuring an image data transfer system, such as, according to one or more of the previously indicated aspects, including in a medical work area, wherein the image data transfer system comprises at least one image data source, at least one image data sink and a connection node, the connection node is coupled to the image data source and the image data sink via at least one data connection respectively, the image data source is configured to provide image data in at least two data formats that are different from one another, and the image data sink is configured to process image data in one of the data formats, wherein information relating to a selection of the image data sink is available in the connection node and the connection node can be configured such that it provides a data transfer path between the selected image data sink and the image data source, wherein the provided data transfer path can be configured in such a way that, from the image data source, image data can be provided to the image data sink in the data format of the image data sink.

The same or similar advantages as have already been mentioned with respect to the image data transfer system also apply to the configuration method.

Still further, such object can be solved by a computer program product comprising a computer-readable medium, on which program instructions are stored, which prompt an image data transfer system according to one or more of the indicated embodiments and aspects to execute a method according to one or more of the aspects indicated above in a medical work area.

BRIEF DESCRIPTION OF THE DRAWINGS

Further features can be seen from the description of embodiments, together with the claims and the appended drawings. Embodiments can fulfil individual features or a combination of multiple features.

The embodiments are described below without restricting the general concept using exemplary embodiments with reference to the drawings, wherein reference is expressly made to the drawings with regard to any details, which are not explained in greater detail in the text, wherein.

DETAILED DESCRIPTION

Figure 1:
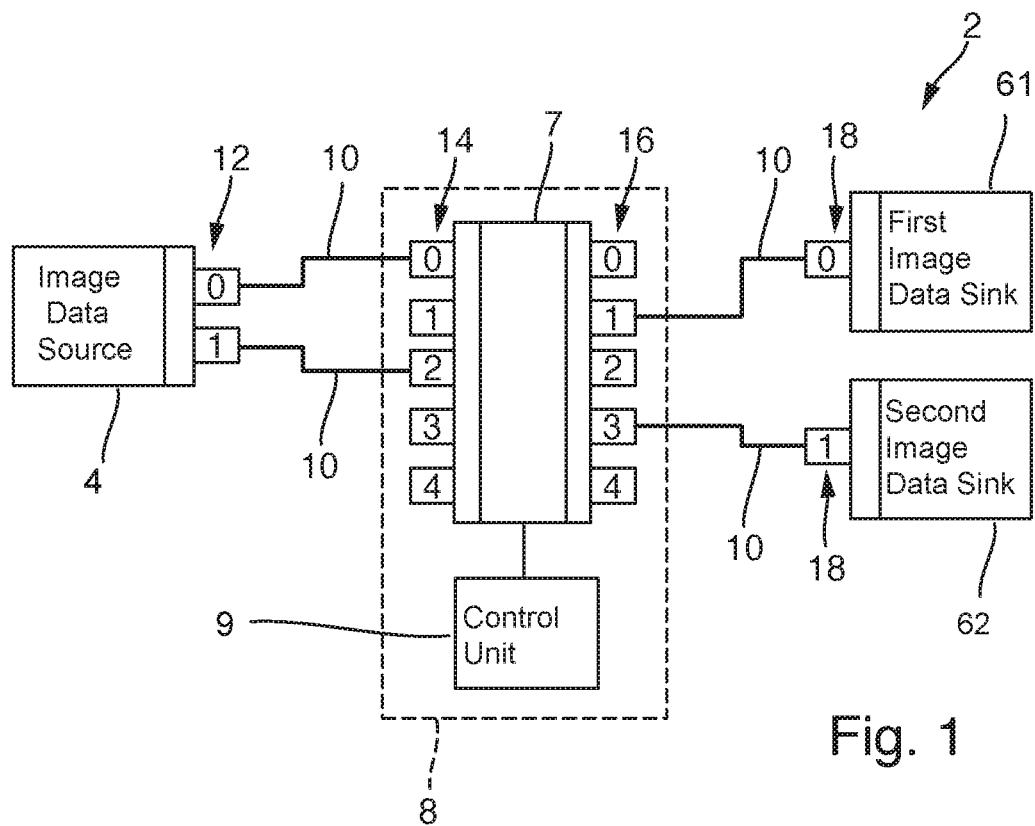
FIG. 1 illustrates an image data transfer system in a schematically simplified representation.

In the drawings, the same or similar elements and/or parts are provided with the same reference numerals so that they are not introduced again in each case.

FIG. 1 shows, in a schematically simplified view, an image data transfer system 2, applied or respectively used by way of example in a medical work area. The image data transfer system 2 comprises an image data source 4. A single image data source 4 is simply shown by way of example in FIG. 1. The image data transfer system 2 additionally comprises a first image data sink 61 and a second image data sink 62. It is likewise envisaged that the image data transfer system 2 simply comprises a single image data sink 61 or 62. The image data source 4 and the image data sinks 61, 62 are coupled to one another via a connection node 8. The connection node 8 comprises a switching matrix 7 and a control unit 9. The switching matrix 7 provides internal data connections between its input-side interfaces 14 and its output-side interfaces 16. The control unit 9 controls the switching matrix.

Interfaces 12 which are present on the image data source 4, and which are identified by "0" and "1" by way of example, are coupled to the input-side interfaces 14 of the connection node 8 via data connections 10. The output-side interfaces 16 of the connection node 8 are also coupled via data connections 10 to the interfaces 18 of the image data sinks 61, 62. The input-side interfaces 14 of the connection node 8 are, by way of example, identified by "0" to "4". The same applies to the output-side interfaces 16. The interface 18 of the first image data sink 61 is identified by "0", while the interface 18 of the second image data sink 62 is identified by "1".

The data connections 10 can be physically realized by a single cable or multiple parallel cables. Four parallel HDMI cables are provided, for example, in order to transfer 4K image data. These individual cables are coupled to one of the inputs or respectively outputs of the connection node 8. Accordingly, the connection node 8 establishes an allocation between multiple input-side interfaces 14 and multiple output-side interfaces 16. The number of the input-side and output-side interfaces 14, 16 can be equally large. For example, four input-side interfaces 14, which are coupled, for example, to four input-side HDMI cables, and also four output-side interfaces 16, which are coupled, for example, to four output-side HDMI cables, are connected.

The image data source 4 is, for example, a camera, which can be provided in a medical or surgical device or respectively instrument. The image data source 4 is configured to provide image data in two data formats that are different from one another to both its interfaces "0" and "1". For example, the image data source 4 is a camera integrated into a stereo video endoscope, which provides both 2D image data and 3D image data. By way of example, 2D image data is provided to the interface 12, which is designated by "0", and 3D image data is provided to the interface 12, which is designated by "1". The image data is, for example, photo or video data, which can be an image data stream.

It is additionally envisaged that the image data source 4 comprises additional interfaces 12 which are not shown, to which image data is provided in other formats. Alternatively or in addition to the provision of 2D and 3D image data, it is likewise envisaged in accordance with other exemplary embodiments that image data, for example of different resolution, is provided to the different interfaces 12 of the image data source 4. Image data in HD or 4K format can be indicated by way of example. One or more cables for transferring data is/are connected to the interfaces 12. For example, an interface for transferring 4K video data comprises four HDMI outputs.

The image data sinks 61, 62 can be, image data reproducing devices, for example, monitors or flat screens. Purely by way of example, the first image data sink 61 can be a screen which is simply configured to reproduce 2D image data. The second image data sink 62 is also, by way of example, a monitor. This can be configured to reproduce 3D image data.

The control unit of the connection node 8 can be, for example, part of a computer or a workstation. In such an exemplary embodiment, the control unit can be realized by software or hardware or a combination of software and hardware. The connection node 8 can be coupled to an operating unit which is not shown in FIG. 1.

The data connections 10 between the interfaces 12 of the image data source 4 and the input-side interfaces 14 of the connection node 8 as well as the data connections 10 between the output-side interfaces 16 of the connection node 8 and the interfaces 18 of the image data sinks 61, 62 are wired or wireless data connections in accordance with commonly used technical standards. The interfaces 12, 14, 16, 18 of the image data source 4 of the connection node 8 and of the image data sinks 61, 62 are serial or parallel interfaces also in accordance with commonly used standards.

A data transfer path is provided in order to transfer data between the data source 4 and the image data sinks 61, 62. The data transfer path comprises the data connection 10 between the interface 12 of the data source 4 and the input-side interface 14 of the switching matrix 7, the internal data connection of the switching matrix 7 between the input-side and output-side interfaces thereof 14, 16 and, finally, the data connection between the output-side interface 16 of the switching matrix and the interface 18 of the image data sink 61, 62.

Figure 2:
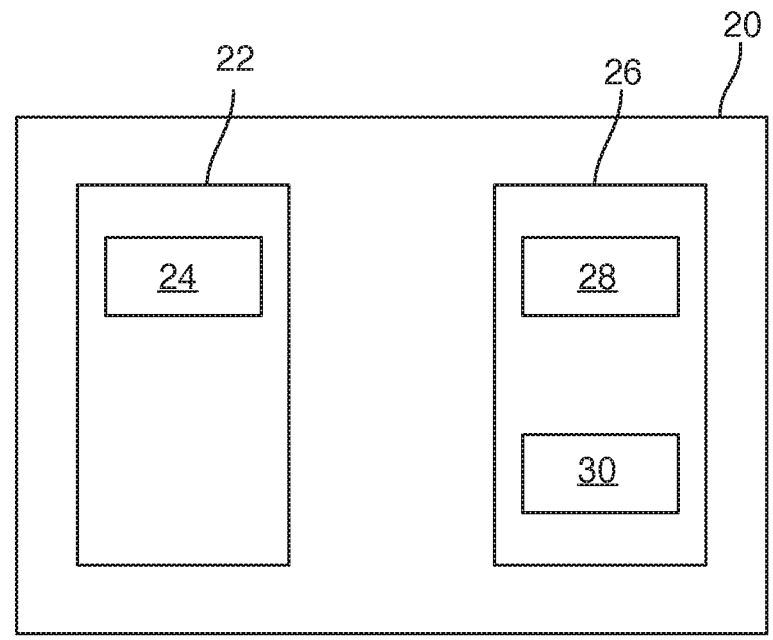
FIG. 2 illustrates a schematically simplified representation of a user interface of such an image data transfer system.

FIG. 2 shows, in a schematically simplified representation, an exemplary view of a user interface of an operating unit 20 connected to the connection node 8. This is, for example, a touch-sensitive screen.

On the left side a first selection field 22 is shown, which serves to select the image data sources 4. By way of example a field, which is e.g. a soft button 24, is shown therein. This soft button is used, by way of example, to select the image is data source 4 shown in FIG. 1. In other words, the user can, for example, select the stereo video endoscope as the image data source 4 with the soft button 24. On the right side of the operating unit 20 a second selection field 26 is shown, which comprises a third and a fourth soft button 28, 30. The second selection field 26 serves to select the image data sinks. The first image data sink 61 is selected, for example with the second soft button 28. This is, for example, the monitor suitable for reproducing 2D image data. In addition, the second image data sink 62 is selected, for example with the soft button 30, where this is, for example, a monitor which is suitable for reproducing 3D image data.

The connection node 8 is therefore configured to obtain information relating to a selection of one of the image data sinks 61, 62, therefore, for example, of the monitor which is suitable for reproducing 2D image data or the monitor which is suitable for reproducing 3D image data. It is likewise envisaged that this information is made known in a different way to the connection node 8, for example by means of a control signal received from another unit. Accordingly, the connection node 8 establishes a data transfer path between the selected image data sink 61, 62 and the image data source 4, wherein said data transfer path is configured in such a way that, from the image data source 4, image data is/can be provided to the image data sink 61, 62 in the format of the selected image data sink 61, 62.

Specifically, this means that if a user actuates the first soft button 28 on the operating unit 20 in the second selection field 26, i.e. selects the first image data sink 61, a corresponding data transfer path between the same and the suitable interface 12 of the image data source 4 is established. The first image data sink 61 is, by way of example, the monitor for reproducing 2D image data. The interface 18, which is identified by "0", is therefore intended to receive 2D image data. From the image data source 4, by way of example a stereo video endoscope, 2D image data is provided to the interface 12 which is designated by "0", and 3D image data is provided to the interface 12 which is designated by "1". The connection node 8 is then configured in such a way that information is available that the same is being provided with 2D image data at its input-side interface 14, designated by "0", and is being provided with 3D image data at its input-side interface 14, designated by "1". The connection node 8 is, for example, able to establish which data format exists at which interface 14, or it has been programmed accordingly during wiring. To this end, a configuration method can serve to configure an image data transfer system 2 according to aspects.

In addition, information is available in the connection node 8 that the image data sink 61, which is coupled to the output-side interface 16, designated by "1", has to be supplied with 2D image data. In this respect, the connection node 8 is, for example, also able to establish which data format is requested at which output-side interface 16 or it has been programmed accordingly during the wiring.

If the connection node 8 obtains, for example by means of an appropriate input at the operating unit 20, the information that the first image data sink 61 has been selected, the connection node 8 establishes a suitable data connection between the image data source 4 and the selected image data sink 61. This means that the connection node 8, more precisely the switching matrix, establishes an internal data connection between the input interface 14, designated by "0", and the output interface 16, designated by "1". It is thus ensured that 2D image data from the interface 12, designated by "0", of the image data source 4 reaches the interface 18, designated by "0" of the first image data sink 61 via the input-side interface 14, designated by "0", of the connection node 8 and the output-side interface 16 thereof, designated by "1".

The situation is similar if the second image data sink 62 is selected at the operating unit 20 by activating the soft button 30. This is, for example, a monitor which is suited to reproducing 3D image data. The connection node 8 receives a corresponding signal which indicates that the second image data sink 62 has been selected. Information should already be available in the connection node 8, by means of the layout of its interfaces 14, 16, that it has, for example, already recognized that 3D image data is being provided from the image data source 4 to its input-side interface 14, designated by "2". In addition, the connection node 8 has, for example, already recognized that the second image data sink 62 is requesting 3D image data at its output-side interface 16, designated by "3". Accordingly, the connection node 8 establishes, on selecting the second image data sink 62, a connection between the input-side interface 14, designated by "2", and the output-side interface 16, designated by "3". 3D image data is thus transferred from the interface 12 of the image data source 4, designated by "1", via the data connection 10 to the input-side interface 14, designated by "2" of the connection node 8 and further via the output-side interface 16, designated by "3", of the connection node 8 and the data connection 10 to the interface 18 of the second image data sink, designated by "1".

The functionality described above of the connection node 8 is realized in the interaction of the control unit 9, which, for example, receives or supplies the relevant information, with the switching matrix 7, which provides the physical connection between the input-side interfaces 14 and the output-side interfaces 16.

As a result, the user of the image data transfer system 2 is provided with extended functionality so that the latter simply has to select the desired image data sink 61, 62, therefore, for example, a monitor which is suitable for reproducing 2D image data or for reproducing 3D image data, and the selection of the technically suitable interface of the image data source 4, for example of a suitable output of a stereo video endoscope, is made automatically, starting from this information. The user is no longer compelled to worry about suitable image formats or image data sources and sinks which are compatible with one another.

Image data in two formats that are different from one another in the exemplary embodiment shown above is simply, by way of example, 2D and 3D image data. Similarly it is envisaged, in accordance with further exemplary embodiments, that image data which is different from one another includes such formats that are different in other ways, and is provided to the image data source and processed by the image data sinks 61, 62. The following should be indicated by way of example: image data of different resolutions such as HD or 4K. Accordingly, the image data source 4 can be, by way of example, a stereo video endoscope which is in a position to provide image data of different resolution to its interfaces 12. Accordingly, the image data sinks 61, 62 can be monitors which are suitable for reproducing, for example, HD or 4K image data. A selection of one of the two monitors as an image data sink would, in turn, prompt the connection node 8 to select the suitable interface 12 of the image data source 4.

Monitors or screens as image reproducing units are simply indicated by way of example as image data sinks 61, 62. It is additionally likewise envisaged that image data memories or image data processing units can be provided as image data sinks 61, 62. The image data is image data of moving or non-moving images, i.e. for example, image data of photos or videos. This applies both to the 2D and to the 3D image data. The image data can be an image data stream.

In a method for transferring image data into an image data transfer system 2, as shown by way of example in FIG. 1, and which can be part of a medical work area, image data is to be transferred, for example, between an image data source 4 and, optionally, one of at least two image data sinks 61, 62. The image data source 4 and the image data sinks 61, 62 are coupled to the connection node 8 via data connections 10.

The image data source 4 provides image data in at least two data formats that are different from one another to its interfaces 12 (for example, 2D image data to interface "0", and 3D image data to interface "1"). The image data sinks 61, 62 are respectively configured to reproduce at least one of these formats. The first image data sink 61 is, by way of example, configured to receive 2D image data at its interface 18, designated by "0", while the second image data sink 62 is configured to receive 3D image data at its interface 18, designated by "1".

In the connection node 8, more precisely in the control unit 9, information is available relating to a selection of one of the two image data sinks 61, 62. This information is received, for example. This is additionally effected, for example, by means of an input by the user at the operating unit 20 and appropriate communication of this signal to the connection node 8.

The connection node 8 subsequently provides a data transfer path between the selected image data sink 61, 62 and the appropriate interface 12 of the image data source 4 such that the data connection 10 is configured to provide, from the image data source 4, image data to the image data sink 61 in the format of the selected image data sink 61.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Image data transfer system
4 Image data source
61 First image data sink
62 Second image data sink
7 Switching matrix
8 Connection node
9 Control unit
10 Data connection
12 Interface of the image data source
14 Input-side interfaces
16 Output-side interfaces
18 Interfaces of the image data sinks
20 Operating unit
22 First selection field
24 First soft button
26 Second selection field
28 Second soft button
30 Third soft button

What is claimed is:

1. An image data transfer system comprising:
at least one image data source;
a plurality of image data sinks; and
a connection node;
wherein the connection node is coupled to the at least one image data source and the plurality of image data sinks via at least one respective data connection;
the at least one image data source is configured to provide image data in a plurality of data formats that are different from one another;
each of the plurality of image data sinks are configured to process image data only in one of the plurality of data formats; and
the connection node comprises a controller configured to:
receive information indicating a selection of one image data sink from the plurality of image data sinks; and
establish a data transfer path between the one image data sink and the at least one image data source, the data transfer path being configured in that, from the at least one image data source, image data is provided to the one image data sink in a data format of the one image data sink.

2. The image data transfer system according to claim 1, wherein the at least one image data source comprises at least two interfaces, to which the image data is provided in one of the plurality of data formats, wherein the connection node comprises input-side interfaces coupled to the at least two interfaces of the at least one image data source via data connections, and output-side interfaces, to which the plurality of image data sinks are coupled via the at least one respective data connection, wherein the connection node is configured to establish an internal data connection between an output side interface of the output-side interfaces coupled to the one image data sink and an input-side interface of the input-side interfaces to which image data is provided in the data format of the one image data sink from the at least one image data source.

3. The image data transfer system according to claim 1, wherein the plurality of image data sinks comprise a first image data sink and a second image data sink, wherein the first image data sink is configured to process image data in a first data format, and the second image data sink is configured to process image data in a second data format that is different from the first data format, wherein the connection node is configured to receive information relating to a selection of the first image data sink or a selection of the second image data sink and to establish a data transfer path between a selected first image data sink or a selected second image data sink and the at least one image data source, wherein the data transfer path is configured in such a way that, from the image data source, image data is provided to the selected first image data sink or the selected second image data sink in the data format of the selected first image data sink or the selected second image data sink.

4. The image data transfer system according to claim 1, wherein the plurality of image data sinks comprise one or more of an image data reproducing unit, an image data memory and an image data processing unit.

5. The image data transfer system according to claim 1, wherein the plurality of data formats are one or more of 2D and 3D image data of one or more of moving and non-moving images and the plurality of image data sinks are configured to process 2D or 3D image data of moving or non-moving images.

6. The image data transfer system according to claim 1, wherein the at least one image data source is a medical device.

7. The image data transfer system according to claim 6, wherein the medical device is selected from a group consisting of a surgical instrument, an endoscope and a stereo endoscope.

8. A connection node for use in an image data transfer system comprising at least one image data source and a plurality of image data sinks, wherein the connection node is coupled to the at least one image data source via at least two input-side interfaces and to the a plurality of image data sinks via at least one respective output-side interface, wherein the at least two input-side interfaces are configured to receive image data in two data formats that are different from one another provided from the at least one image data source coupled to the respective interface, and the output-side interface is configured to provide image data in a data format of the plurality of image data sinks, wherein the at least one image data sink is configured to process image data of the data format, that the connection mode comprising:
  a controller configured to:
    provide information relating to a selection of one image data sink of the plurality of image data sinks; and
    establish an internal data connection between the output-side interface, to which the one image data sink is coupled, and the input-side interface, to which image data from the at least one image data source is provided in a data format of the one image data sink.

9. A medical work area system comprising:
  an image data transfer system according to claim 1;
  wherein the at least one image data source is a medical device.

10. The medical work area system according to claim 1, wherein the medical device is selected from a group consisting of a surgical instrument, an endoscope and a stereo endoscope.

11. A method for transferring image data between an image data source and a plurality of image data sinks, the method comprising:
  coupling the image data source to the plurality of image data sinks via a connection node, where the image data source is configured to provide image data in a plurality of data formats that are different from one another and the plurality of image data sinks are configured to process image data in one of the plurality of data formats;
  providing information relating to a selection of one image data sink of the plurality of image data sinks in the connection node; and
  establishing a data transfer path between the one image data sink and the image data source, wherein the data transfer path is configured in such a way that, from the image data source, image data is provided to the one image data sink in a data format of the one image data sink.

12. The method according to claim 11, wherein the image data source comprises at least two interfaces, to which the image data is provided in one of the plurality of data formats that are different from one another respectively, wherein the connection node comprises input-side interfaces, each of which being coupled to one of the at least two interfaces of the image data source via at least one data connection respectively, and output-side interfaces, to which the plurality of image data sinks are coupled via at least one respective data connection, and wherein the connection node establishes an internal data connection between an output-side interface of the output side interfaces connected to the one image data sink and an input-side interface of the input side interfaces, to which image data in the data format of the one image data sink is provided from the image data source.

13. The method according to claim 11, wherein the plurality of image data sinks comprise a first image data sink and a second image data sink, wherein the first image data sink processes image data in a first data format and the second image data sink processes image data in a second data format that is different from the first data format, wherein the connection node receives information relating to a selection of the first image data sink or a selection of the second image data sink, and establishes a data transfer path between a selected first image data sink or a selected second image data sink, wherein the data transfer path is configured in such a way that, from the image data source, image data is provided to the selected first image data sink or the selected second image data sink in the data format of the selected first image data sink or the selected second image data sink.

14. A computer program product comprising a computer-readable medium, on which program instructions are stored, which prompt an image data transfer system to execute the method according to claim 11 in a medical work area.

\* \* \* \* \*